US009688655B2

(12) United States Patent
Haim et al.

(10) Patent No.: US 9,688,655 B2
(45) Date of Patent: Jun. 27, 2017

(54) PROCESS FOR THE PREPARATION OF A DIARYLTHIOHYDANTOIN COMPOUND

(71) Applicant: Aragon Pharmaceuticals, inc., San Diego, CA (US)

(72) Inventors: Cyril Ben Haim, Beerse (BE); Andras Horvath, Turnhout (BE); Johan Erwin Edmond, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/973,089

(22) Filed: Dec. 17, 2015

(65) Prior Publication Data
US 2016/0176845 A1 Jun. 23, 2016

Related U.S. Application Data

(60) Provisional application No. 62/094,436, filed on Dec. 19, 2014.

(51) Int. Cl.
*C07D 401/04* (2006.01)
*C07D 213/61* (2006.01)
*C07D 213/84* (2006.01)

(52) U.S. Cl.
CPC ......... *C07D 401/04* (2013.01); *C07D 213/61* (2013.01); *C07D 213/84* (2013.01)

(58) Field of Classification Search
CPC .................................................. C07D 401/04
USPC ........................................................ 546/15
See application file for complete search history.

(56) References Cited

U.S. PATENT DOCUMENTS 8,987,452 B2 *  3/2015  Ouerfelli ............... C07C 209/36
                                                    546/15
2004/0077605 A1    4/2004  Salvati

FOREIGN PATENT DOCUMENTS

| CA | 2908326 A1 | 4/2014 |
| WO | 2007126765 A2 | 8/2007 |
| WO | 2008119015 A2 | 2/2008 |
| WO | 2009140624 A2 | 11/2009 |
| WO | 2011069951 A1 | 6/2011 |
| WO | 2013029338 A1 | 7/2013 |

OTHER PUBLICATIONS

Ivachtchenko, Alexandre, V. et al: Design, synthesis and biological evaluation of novel 5-oxo-2-thioxoimidazolidine dertivatives as potent androgen receptor antagonists, European Journal of Medicinal Chemistry, vol. 99, Jun. 2, 2015, pp. 51-66, XP029222670.
International Search Report and Written Opinion for Application No. PCT/US2015/066356 mailed Jul. 5, 2015.

* cited by examiner

*Primary Examiner* — Patricia L Morris

(57) ABSTRACT

Disclosed are processes and intermediates for the preparation of compound (X), which is currently being investigated for the treatment of prostate cancer.

22 Claims, No Drawings

PROCESS FOR THE PREPARATION OF A DIARYLTHIOHYDANTOIN COMPOUND

CROSS-REFERENCE TO RELATED APPLICATIONS

This Application claims priority to U.S. Provisional Patent Application No. 62/094,436, filed Dec. 19, 2014, which is hereby incorporated by reference in its entirety.

STATEMENT REGARDING FEDERALLY SPONSORED RESEARCH OR DEVELOPMENT

The research and development of the invention described below was not federally sponsored.

FIELD OF THE INVENTION

The present invention is directed to the preparation of compound (X) and intermediates in its synthesis. More specifically, the present invention is directed to processes for the preparation of compound (X), disclosed in U.S. Pat. No. 8,445,507, issued on May 21, 2013, which is hereby incorporated by reference in its entirety.

BACKGROUND OF THE INVENTION

Compound (X) of the present invention is currently being investigated for the treatment of prostate cancer. The present invention describes a process and intermediates for the preparation of such compound.

SUMMARY OF THE INVENTION

The present invention is directed to a process for the preparation of compound (X)

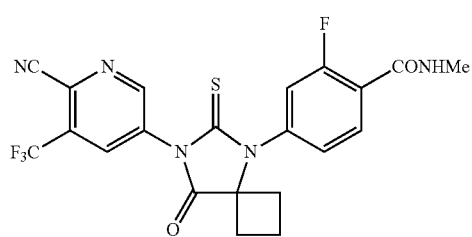

(X)

comprising, consisting of and/or consisting essentially of

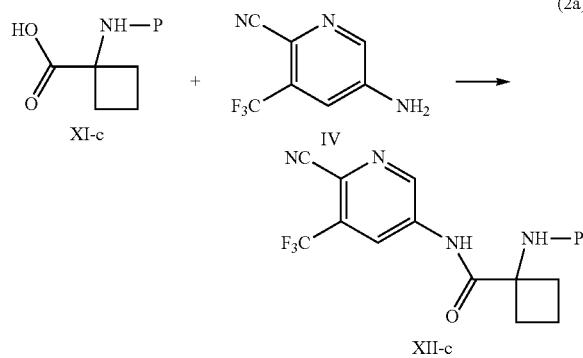

(2a)

(i) reacting a compound of formula (XI-c), wherein P is a suitable amino protecting group, with compound (IV) under amide-bond formation conditions; in the presence of an amide coupling reagent; and in the presence of a catalyst; in an organic solvent; at a temperature in the range of from about 0° C. to about 50° C.; to yield the corresponding compound of formula (XII-c); or,

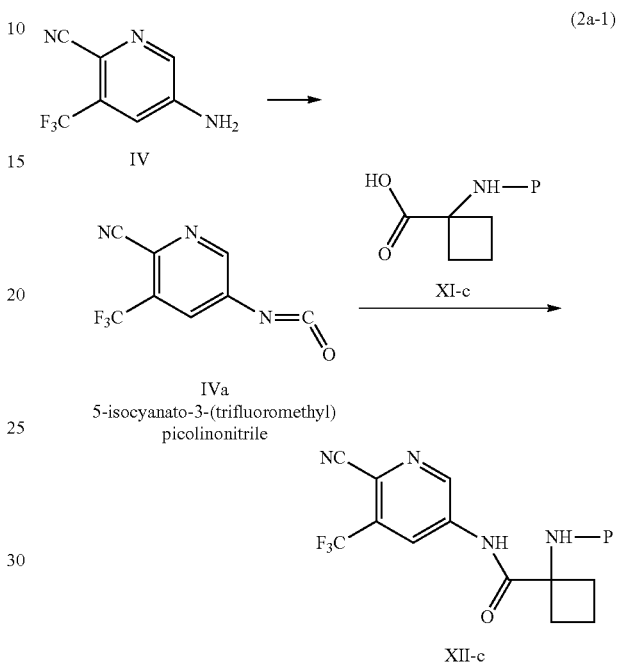

(2a-1)

IVa
5-isocyanato-3-(trifluoromethyl)picolinonitrile (ii) reacting compound (IV) with phosgene or a phosgene analog; in the presence of an organic base; in an aprotic solvent; then treating a resulting isocyanate intermediate (IVa), optionally without isolation, with a compound of formula (XI-c); in the presence of a non-nucleophilic base; at a temperature in the range of from about −20° C. to about 80° C.; to yield the corresponding compound of formula (XII-c);

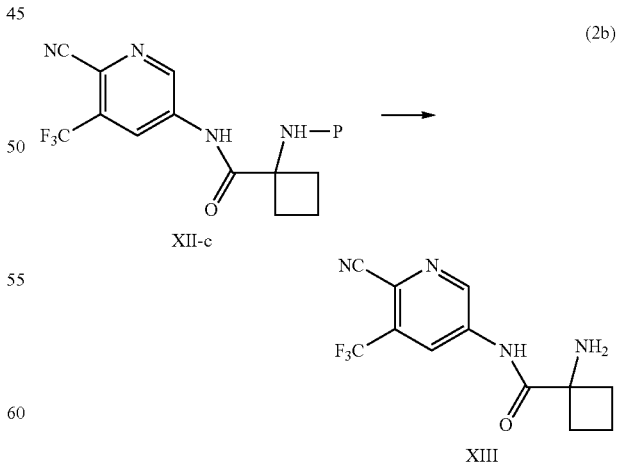

(2b)

reacting a compound of formula (XII-c) under suitable amino deprotection conditions; in an organic solvent; at a temperature greater than ambient temperature; to yield the corresponding compound (XIII);

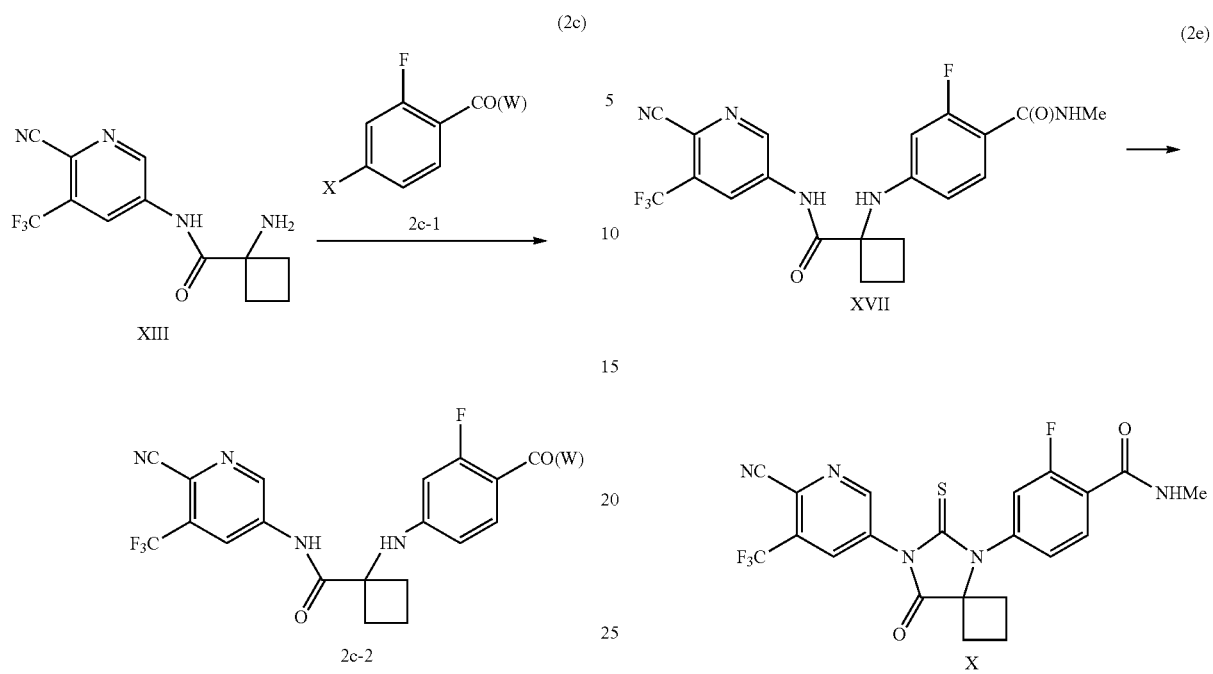

reacting compound (XIII) with a compound of formula (2c-1) wherein X is chloro, bromo, or iodo and W is $C_{1-8}$alkoxy or methylamino; in the presence of a Cu(0) source or a copper salt; in the presence of an inorganic base; in an organic solvent; optionally in the presence of a ligand; optionally in the presence of a suitable reducing agent; at a temperature in the range of from about room temperature to about 140° C.; to yield the corresponding compound of formula (2c-2) wherein W is $C_{1-8}$alkoxy or methylamino;

reacting compound (XVII) with a thiocarbonyl source; in the presence of an activating agent; in an organic solvent; optionally in the presence of an organic base; at a temperature in the range of from about −20° C. to about 100° C.; to yield the corresponding compound (X).

In another embodiment, a compound of formula (2c-2B), wherein W is $C_{1-8}$alkoxy, is converted to a compound of formula (2e), as shown in scheme (2f), by

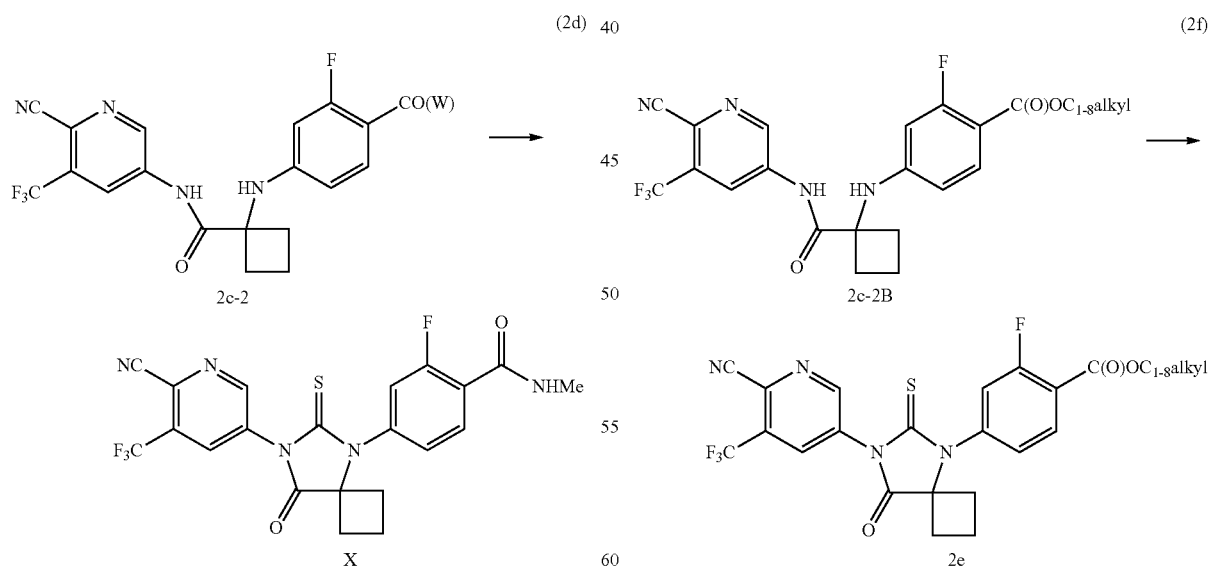

converting a compound of formula (2c-2) to compound (X), discussed in further detail below.

In one embodiment, compound (XVII), wherein W is methylamino, is converted to compound (X), as shown in scheme (2e), by reacting a compound of formula (2c-2B) with a thiocarbonyl source; in the presence of an activating agent; in an organic solvent; at a temperature in the range of from about −20° C. to about 100° C.; to yield the corresponding compound of formula (2e); then

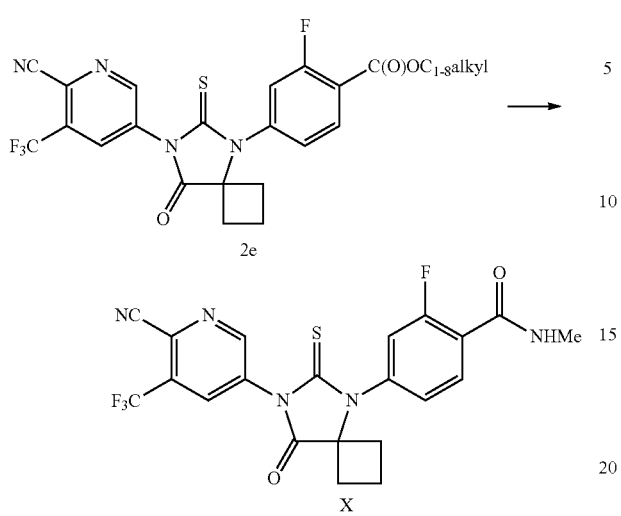

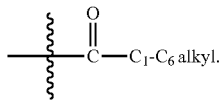

treating a compound of formula (2e) with methylamine; in an organic solvent; at about ambient temperature; to yield the corresponding compound (X).

DETAILED DESCRIPTION OF THE INVENTION

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, $(C_{1-6}alkyl)_2amino$-, the $C_{1-6}$alkyl groups of the dialkylamino may be the same or different.

The term "alkoxy" refers to an —O-alkyl group, wherein the term "alkyl" is as defined above.

The term "cycloalkyl" refers to a saturated or partially saturated, monocyclic hydrocarbon ring of 3 to 8 carbon atoms. Examples of such rings include cyclopropyl, cyclobutyl, cyclopentyl, cyclohexyl, and cycloheptyl.

The term "aryl" refers to an unsaturated, aromatic monocyclic or bicyclic ring of 6 to 10 carbon members. Examples of aryl rings include phenyl and naphthalenyl.

The term "halogen", "halide", or "halo" refers to fluorine, chlorine, bromine and iodine atoms.

The term "carboxy" refers to the group —C(=O)OH.
The term "formyl" refers to the group —C(=O)H.
The term "oxo" or "oxido" refers to the group (=O).
The term "thiono" refers to the group (=S).
The term "room temperature" or "ambient temperature", as used herein refers to a temperature in the range of from about 18° C. to about 22° C.

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

$$\overset{O}{\underset{}{\|}}{-}C{-}C_1\text{-}C_6\,alkyl.$$

Abbreviations used in the instant specification, particularly the schemes and examples, are as follows:

ABBREVIATIONS

ACN acetonitrile
aq aqueous
Boc tert-butoxycarbonyl
CDI 1,1'-carbonyldiimidazole
DABCO 1,4-diazabicyclo[2.2.2]octane
DBN 1,5-diazabicyclo(4.3.0)non-5-ene
DBU 1,8-diazabicyclo[5.4.0]undec-7-ene
DCM dichloromethane
DIEA or DIPEA diisopropylethylamine
DMA dimethylacetamide
DMAPA dimethylaminopropylamine or $N^1,N^1$-dimethylpropane-1,3-diamine
DMAP 4-(dimethylamino)pyridine
DMF dimethylformamide
DMSO dimethyl sulfoxide
DMTMM 4-(4,6-dimethoxy-1,3,5-triazin-2-yl)-4-methylmorpholinium chloride

ABBREVIATIONS dppf 1,1'-bis(diphenylphosphino)ferrocene
EDCI 1-ethyl-3-(3-dimethylaminopropyl)carbodiimide
EEDQ 2-ethoxy-1-ethoxycarbonyl-1,2-dihydroquinoline
h hour(s)
HCl hydrochloric acid
HPLC high performance liquid chromatography
iPrOAc isopropylacetate
LiHMDS lithium hexamethyldisilazide
Me methyl
MeCN acetonitrile
MEK methyl ethyl ketone
MeOH methyl alcohol
mg milligram
MTBD 9-methyl-2,3,4,6,7,8-hexahydropyrimido[1,2-α]pyrimidine
NMP N-methyl-2-pyrrolidone
PdCl$_2$(dppf) CH$_2$Cl$_2$ 1,1'-bis(diphenylphosphino)ferrocene-palladium(II)dichloride dichloromethane complex)
P(o-tol)$_3$ tri(o-tolyl)phosphine
rt room temperature
T3P propylphosphonic anhydride
TBD 1,5,7-triazabicyclo[4.4.0]dec-5-ene
TCDI 1,1'-thiocarbonyl-di-imidazole
THF tetrahydrofuran
TMEDA N,N,N',N'-tetramethylethylenediamine TMG tetramethylguanidine
2-MeTHF 2-methyl tetrahydrofuran General Schemes The overall scheme for the invention is illustrated in Scheme A, below.

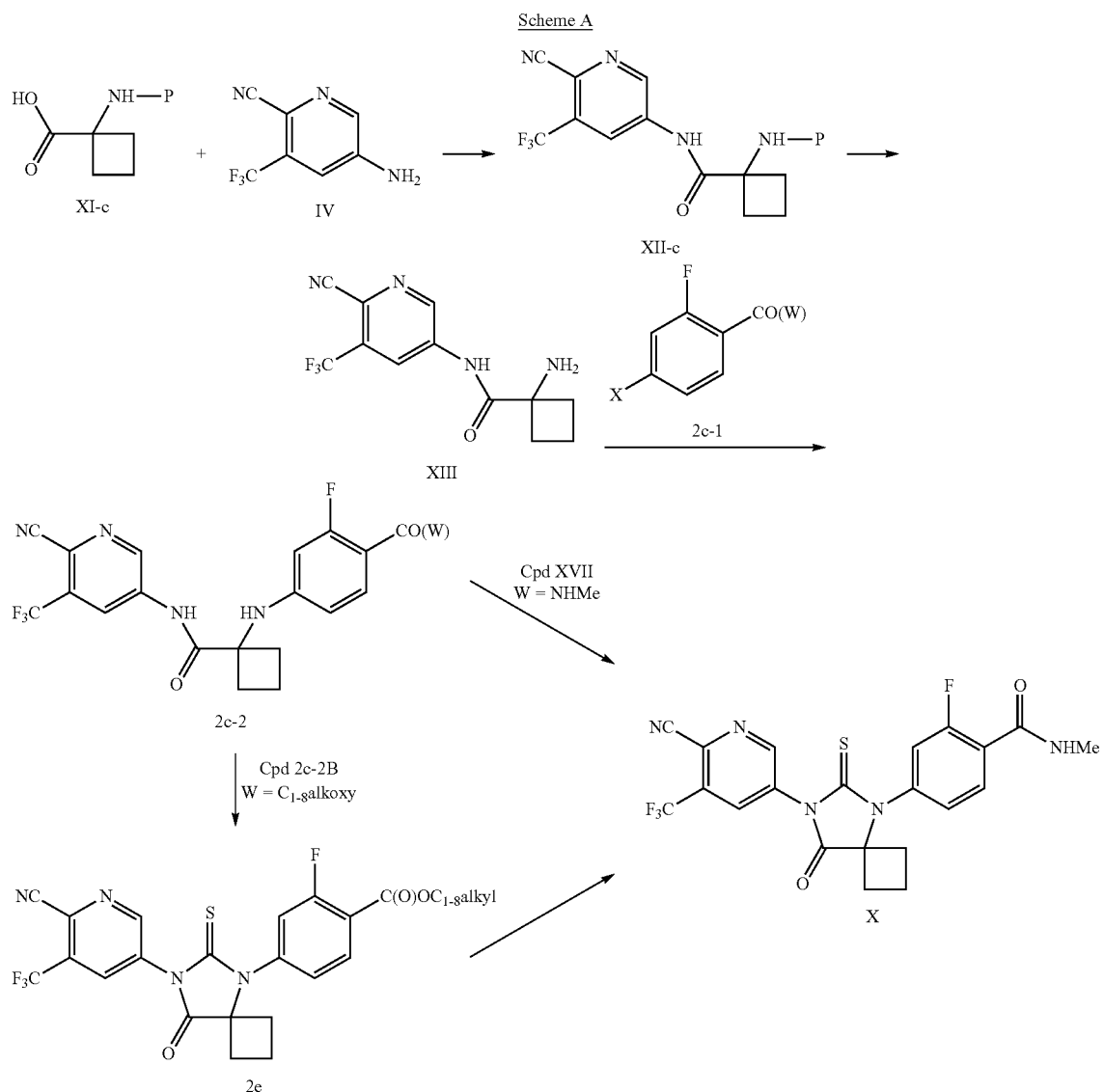

In Scheme A, a compound of formula (XI-c) possesses group P, a conventional amino protecting group such as a carbamate (—NHCO₂R) wherein R is $C_{1-8}$alkyl, phenyl, aryl($C_{1-8}$)alkyl, or the like. A compound of formula (XI-c) may be reacted with compound (IV) under amide-bond formation conditions in the presence of an amide coupling reagent selected from 1,1-carbonyldiimidazole, T3P, EDCI, DMTMM, EEDQ, or the like; in the presence of a catalyst that may be (1) an amidine such as DBU or DBN, (2) a tertiary amine such as DABCO, triethylamine, or DIPEA, (3) a guanidine such as TBD, TMG, or MTBD, or (4) a base such as NaH, KOtBu, and LiHMDS, or the like; in an aprotic solvent such as toluene, MeTHF, THF, iPrOAc, or DCM; or a protic solvent such as IPA or the like; at a temperature in the range of from about 0° C. to about 50° C.; to yield the corresponding compound of formula (XII-c). One of ordinary skill in the art will recognize that some reagents and bases may not be compatible with every solvent disclosed herein, but reagent and base compatibility may be readily identified using knowledge either already known or available in the scientific literature.

In one embodiment, the amide coupling agent is 1,1-carbonyldiimidazole and the catalyst is DBU.

Alternatively, compound (IV) may be treated first with either phosgene or a phosgene analog selected from triphosgene (bis(trichloromethyl) carbonate), diphosgene (trichloromethyl chloroformate), or the like; in the presence of a tertiary amine base selected from triethylamine, ethyl diisopropylamine, or DABCO; in an aprotic solvent selected from DCM, toluene, THF, or MeTHF; at a temperature in the range of from about −20° C. to about 50° C.; to form 5-isocyanato-3-(trifluoromethyl)picolinonitrile (IVa) as an intermediate. Reaction of intermediate (IVa) with compound (XI-c); in the presence of a non-nucleophilic base that is (1) an amidine such as DBU or DBN, (2) a tertiary amine such as DABCO or triethylamine, or (3) a guanidine such as TBD, TMG, or MTBD; at a temperature in the range of from about −20° C. to about 80° C.; to yield the corresponding compound of formula (XII-c).

The amino group of a compound of formula (XII-c) may be deprotected using conventional methods such as under acidic conditions in an organic solvent such as isopropanol, toluene, MeTHF, THF, iPrOAc, DCM, IPA, water, or the like; at a temperature greater than ambient temperature; to yield the corresponding compound (XIII).

Compound (XIII) may be reacted with a compound of formula (2c-1) wherein X is chloro, bromo, or iodo and W is $C_{1-8}$alkoxy or methylamino; in the presence of either (1) a Cu(0) source such as copper powder or copper sponge, or (2) a copper salt selected from cuprous chloride, cuprous iodide, cuprous bromide, cuprous acetate, or cupric bromide; in the presence of an inorganic base such as potassium acetate, potassium carbonate, cesium carbonate, CsF, sodium pivalate, or the like; in an organic solvent such as DMF, DMA, DMSO, acetonitrile, propionitrile, butyronitrile, or an alcoholic solvent such as amyl alcohol; with or without the addition of a Cu (I) salt selected from cuprous chloride, cuprous iodide, cuprous bromide, or cuprous acetate; and optionally in the presence of a ligand such as 2-acetylcyclohexanone, TMEDA, or phenanthroline; and optionally in the presence of a reducing agent such as sodium ascorbate or sodium bisulfite; at a temperature in the range of from about room temperature to about 140° C.; to yield the corresponding compound of formula (2c-2) wherein W is $C_{1-8}$alkoxy or methylamino.

In one embodiment, the copper salt is cuprous bromide and the ligand is TMEDA.

In another embodiment, the Cu(0) source is copper powder.

In another embodiment, the Cu(0) source is copper sponge.

In a further embodiment, the organic solvent is DMA.

In a further embodiment, the organic solvent is DMSO.

In another embodiment, the reaction of compound (XIII) with a compound of formula (2c-1) comprises, consists of, and/or consists essentially of, a copper salt such as cuprous bromide with the ligand TMEDA; in the presence of the inorganic base potassium acetate; in an organic solvent such as DMA; at a temperature range of from about 80° C. to about 140° C.

In another embodiment, the reaction of compound (XIII) with a compound of formula (2c-1) comprises, consists of, and/or consists essentially of, a Cu(0) source such as copper powder or copper sponge; in the presence of an inorganic base such as potassium acetate or sodium pivalate; in DMSO; at a temperature in the range of from about 0° C. to about 80° C.

In another embodiment, the reaction of compound (XIII) with a compound of formula (2c-1) comprises, consists of, and/or consists essentially of, a Cu (0) source such as copper powder or copper sponge; in the presence of an inorganic base such as potassium acetate; with the addition of a copper (I) salt selected from cuprous chloride, cuprous iodide, cuprous bromide, or cuprous acetate; in an organic solvent such as DMSO; at a temperature in the range of from about 0° C. to about 80° C.

The present invention further includes processes for the conversion of a compound of formula (2c-2) to compound (X), described in detail as follows.

Compound (XVII), wherein W is methylamino, may be reacted with a thiocarbonyl source selected from O,O'-di(pyridin-2-yl)carbonothioate, 1,1'-thiocarbonylbis(pyridin-2 (1H)-one), di(1H-imidazol-1-yl)methanethione, thiophosgene, an aryl thionochloroformate (wherein aryl is phenyl, naphthyl, or tolyl), or thiocarbonyl bis(benzotriazole); in the presence of an activating agent selected from DMAP, NaH, or NaOH; in an organic solvent selected from DMA, DMF, toluene, DMSO, ACN, THF, DCM, EtOAc, acetone, MEK, or dioxane; optionally in the presence of an organic base selected from triethylamine or DIPEA; at a temperature in the range of from about −20° C. to about 100° C.; to yield the corresponding compound (X).

In one embodiment, the thiocarbonyl source is 1,1'-thiocarbonylbis(pyridin-2(1H)-one).

In another embodiment, the activating agent is DMAP.

In another embodiment, the organic solvent is DMA.

In a further embodiment, the thiocarbonyl source is phenyl thionochloroformate; the activating agent is DMAP; the organic base is selected from triethylamine or DIPEA; the organic solvent is DMA; and at a temperature in the range of from about −20° C. to about 80° C.

In another embodiment, phenyl thionochloroformate may react with DMAP to form an isolatable quaternary salt, compound (S1), shown below.

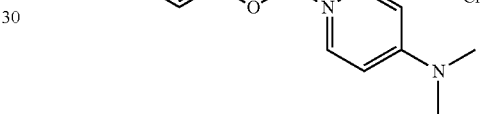

The present invention is further directed to a process comprising, consists of, or consists essentially of reacting compound (XVII) with compound S1; in the presence of an organic base selected from triethylamine or DIPEA; in the organic solvent DMA; at a temperature in the range of from about −20° C. to about 80° C.; to yield the corresponding compound (X).

A compound of formula (2c-2B), wherein W is $C_{1-8}$alkoxy, may be reacted with a thiocarbonyl source selected from O,O'-di(pyridin-2-yl)carbonothioate, 1,1'-thiocarbonylbis(pyridin-2(1H)-one), di(1H-imidazol-1-yl) methanethione, thiophosgene, an aryl thionochloroformate (wherein aryl is phenyl, naphthyl, or tolyl), or thiocarbonyl bis(benzotriazole); in the presence of an activating agent selected from DMAP, NaH, or NaOH; in an organic solvent selected from dimethylacetamide, DMF, toluene, DMSO, THF, or dioxane; optionally in the presence of an organic base selected from triethylamine or DIPEA; at a temperature in the range of from about −20° C. to about 100° C.; to yield the corresponding compound (X).

In one embodiment, W of a compound of formula (2c-2B) is methoxy, designated as compound (XV).

The present invention is further directed to a process including reacting compound (2c-2B) with compound S1; in the presence of an organic base selected from triethylamine or DIPEA; in the organic solvent DMA; at a temperature in the range of from about −20° C. to about 80° C.; to yield the corresponding compound (X).

The compound of formula (2e) may be treated with methylamine; in an organic solvent selected from THF, DMF, DMA, ethanol, or an aqueous mixture thereof; at about ambient temperature; to yield the corresponding compound (X).

In one embodiment, the organic solvent is ethanol.

In another embodiment, the reaction conditions selected from F1 to F11, shown in Table 1, may be used for the conversion of Cpd (2c-2) to either compound (X) or a compound of formula (2e), wherein W is methylamino or $C_{1-8}$alkoxy, respectively.

TABLE 1

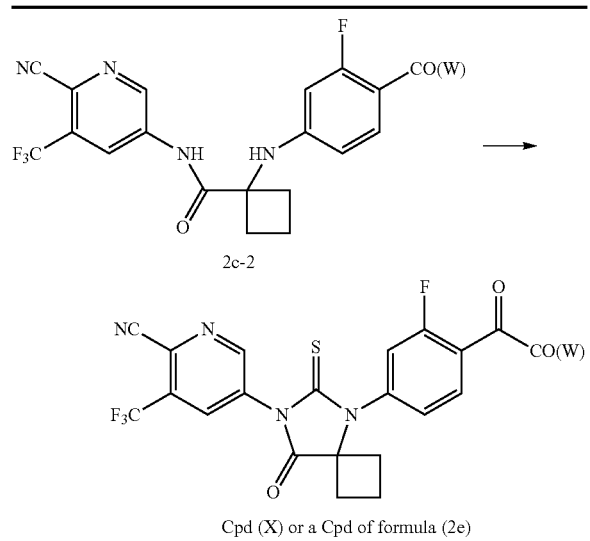

2c-2

Cpd (X) or a Cpd of formula (2e)

| Reaction Conditions | Thiocarbonyl source | Solvent | Activating Agent/ Base | T (° C.) |
|---|---|---|---|---|
| F1 | Thiophosgene | THF | NaOH | −20 to RT |
| F2 | Thiophosgene | THF | DMAP | −20 to RT |
| F3 | Phenyl thionochloroformate | EtOAc | DMAP + Et$_3$N | −20 to 80 |
| F4 | Phenyl thionochloroformate | DMA | DMAP + DIPEA | −20 to RT |
| F5 | Phenyl thionochloroformate | one of THF MeCN, acetone, MEK, DMA or DCM | DMAP + Et$_3$N | −20 to 70 |
| F6 | Phenyl thionochloroformate | toluene | DMAP + Et$_3$N | −20 to 50 |
| F7 | O,O'-di(pyridin-2-yl)carbonothioate | DMA | DMAP | RT to 100 |
| F8 | 1,1'-thiocarbonyl bis(pyridin-2(1H)-one) | DMA | DMAP | RT to 100 |
| F9 | 1,1'-thiocarbonyl bis(pyridin-2(1H)-one) | toluene | DMAP | 60 to 100 |
| F10 | di(1H-imidazol-1-yl)methanethione | DMA | DMAP | RT to 100 |
| F11 | di(1H-benzotriazol-1-yl)methanethione | DMA | DMAP | RT to 100 |

In another embodiment, when the thiocarbonyl source is phenyl thionochloroformate, immediately after cyclization, DMAPA may be added.

SPECIFIC EXAMPLES

The following Examples are set forth to aid in the understanding of the invention, and are not intended and should not be construed to limit in any way the invention set forth in the claims that follow thereafter.

In the Examples that follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

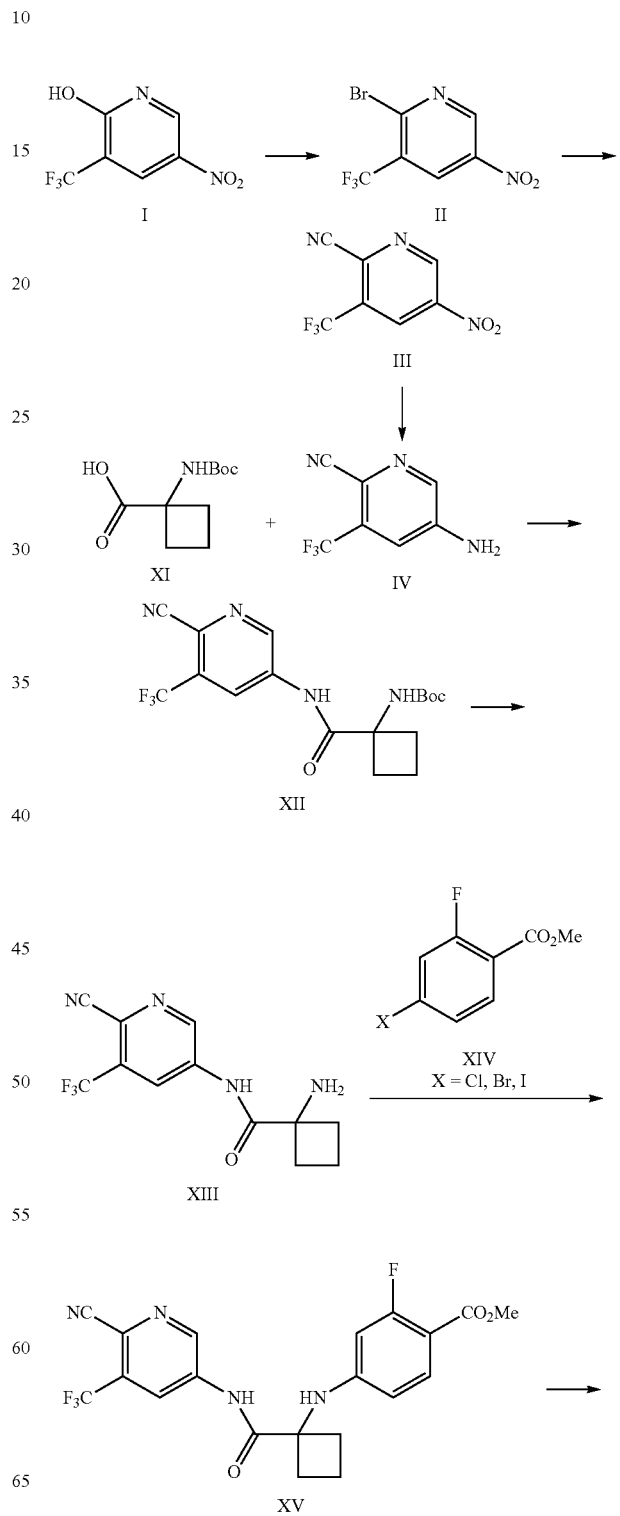

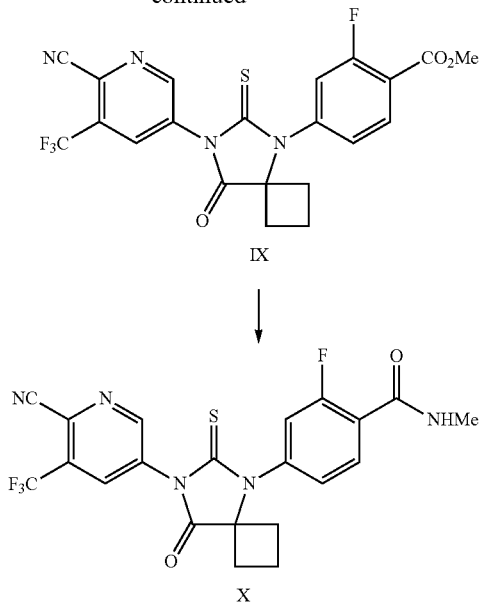

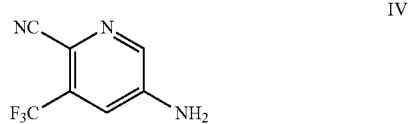 [SMILES: N#Cc1ncc(N)cc1C(F)(F)F]

Step C. Preparation of Compound (IV)

Preparation of Modified Catalyst Slurry.

In a 20 mL beaker glass 0.156 g (0.129 mL, 50 w/w) of $H_3PO_2$ was added to a slurry of 1.00 g 5% Pt/C catalyst F101 R/W (from Evonik AG, contains ~60% water) and 4.0 mL of deionized water. After 15 minutes while stirring with a magnetic stirring bar, 58 mg of $NH_4VO_3$ was added and the slurry was again stirred for 15 minutes.

Hydrogenation.

A 100 mL autoclave was charged with a solution of 10.0 g of compound (III) (46.1 mmol) in 26.7 mL of xylenes and 13.3 mL of butyronitrile. To this solution, the modified catalyst slurry was added with the aid of 2 mL of deionized water. The autoclave was closed, then inertized by pressurizing 3 times with nitrogen to 10 bar and 3 times hydrogen to 10 bar. The reactor pressure was set to 5.0 bar hydrogen, stirring was started (hollow shaft turbine stirrer, 1200 rpm) and the mixture heated up to 70° C. within 50 min. As soon as 70° C. was reached, the hydrogen uptake ceased. After stirring for another 40 min, the heating was stopped and the autoclave was allowed to cooling. The slurry was filtered through a fiberglass filter and washed in portions using 40 mL of xylenes at 20-23° C. Compound (IV) was crystallized from the solution upon distillation of the butyronitrile solvent. $^1$H NMR (300 MHz, DMSO-$d_6$) δ 8.20 (d, J=2.4 Hz, 1H), 7.31 (d, J=2.6 Hz, 1H), 7.04 (s, NH).

Step D. Preparation of Compound (XII)

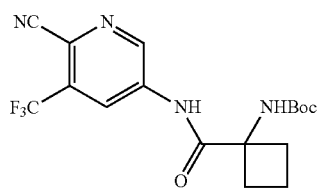

Method A. To a mixture of 18 g (96.2 mmol) of compound (IV), 24.8 g (109.7 mmol) of compound (XI) in 54 mL of tetrahydrofuran (THF) was added 18.5 mL (106 mmol) of N,N-diisopropylethylamine (DIPEA) and 17 g (104 mmol) of carbonyldiimidazole (CDI) in portions at 20° C. The mixture was heated to 60° C. and 15.4 g (101 mmol) 1,8-diazabicyclo[5.4.0]undec-7-ene (DBU) was added. After 2 h, the mixture was diluted with 108 mL of tetrahydrofuran (THF) and washed with an aqueous solution of citric acid (50 g in 72 mL water). Subsequently, the water was partitioned away from the organic layer by means of an azeotropic distillation. Compound (XII) in THF was used as Step A. Preparation of Compound II

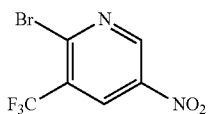

A vessel was charged with 19 g of compound (I), 5 g of triethylamine hydrobromide, 49 g of xylenes and 67 g DMF. A solution of 26 g of phosphorous oxybromide in 16 g of xylene was dosed into the reaction mixture. The reaction mixture was heated to 100° C. for 3 h. The mixture was then cooled to 70° C. To this mixture was added 75 g of a solution of NaOH (10M). After phase separation at room temperature, the organic layer was washed with a 84 g of an aqueous solution of NaOH (10M) followed by 84 g of an aqueous solution of NaCl (25%). The organic phase was carried forward into the next step without further purification. Isolation by crystallization from heptane was performed for characterization purposes of compound (II). $^1$H NMR (300 MHz, CDCl$_3$) δ 9.36, 8.75.

Step B. Preparation of Compound III

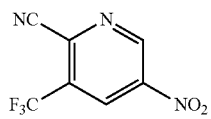

To the previous solution of compound (II) in xylenes was added 8.7 g of sodium cyanide and 6.8 g of copper (I) iodide and 45 g of butyronitrile. The mixture was heated to 120° C. for 20 h. The reaction mixture was cooled, washed twice with an aqueous solution of sodium carbonate (10%). The organic phase was carried forward into the next step. Isolation was performed for characterization purposes of compound (III). $^1$H NMR (300 MHz, DMSO-$d_6$) δ 149.3, 145.4, 133.9, 131.9, 130.1, 119.5, 114.0.

such in the next step. A small sample was isolated for characterization purposes. ¹H-NMR (300 MHz, CDCl₃) δ 10.4 (s, 1H), 8.74 (s, 2H), 5.18 (s, 1H), 2.79 (m, 2H), 2.22 (m, 2H), 2.12 (m, 2H), 1.49 (s, 9H); ¹³C NMR (CDCl₃, JMOD) δ 172.7, 143.6, 138.2, 131.0, 123.5, 123.3, 114.4, 82.2, 59.9, 30.7, 28.3, 15.1.

Method B. To a mixture of 40 g (214 mmol) of compound IV, 37.8 g (233 mmol) of carbonyldiimidazole (CDI, 109.7 mmol) in 120 mL of tetrahydrofuran (THF) was added a solution of 55 g (244 mmol) of compound (XI) in 240 mL of tetrahydrofuran (THF). The mixture was heated to 60° C. and 33.7 mL (224 mmol) 1,8-diazabicyclo[5.4.0]undec-7-ene (DBU) was added. After 4 h, the mixture was washed with an aqueous solution of citric acid (112 g in 160 mL of water). After phase separation at 50° C., the water was separated from the organic layer by means of an azeotropic distillation. Compound (XII) in THF was used as such for the next step.

Step E. Preparation of Compound (XII) via 5-isocyanato-3-(trifluoromethyl) picolinonitrile, (IVa)

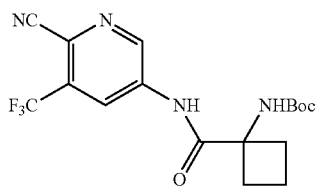

A reactor was charged with 0.2 g (1.1 mmol) of compound (IV), 6 mL of dry DCM, and cooled to 0° C. Triphosgene (0.22 g, 0.67 eq) was added, followed by dropwise addition of triethylamine (0.55 g, 5 eq). The mixture was stirred at 0° C., and after 2 h, compound (IV) was completely converted into compound (IVa) according to HPLC analysis. Compound (XI) (0.28 g, 1.2 eq) was added and the mixture was stirred further at 0° C. HPLC analysis after 1 h showed 42% conversion to compound (XII) in the mixture.

Step F. Preparation of Compound (XIII)

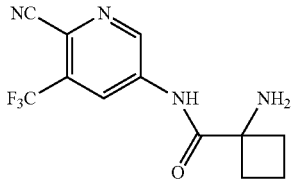

A 6 M solution of hydrochloric acid in isopropanol (2 eq.) was added to solution of compound (XII) in THF. The stirred reaction solution was heated to 70° C. for 5 h. After reaction completion, the mixture is further heated to reflux and switched with 2-propanol. The reaction was allowed to cool to 30° C. and a solution of ammonium hydroxide (3 eq.) was added. The mixture was stirred for 1 h then cooled to 5° C. A precipitate was collected by filtration. The filter cake was washed once with water and once with cold isopropanol. The filter cake was dried under partial vacuum at 50° C. to form compound (XIII) in 80% yield. ¹H NMR (300 MHz, CDCl₃) δ 10.2 (s, 1H), 8.84 (s, 2H), 2.81 (m, 2H), 2.13 (m, 2H), 2.07 (m, 2H); ¹³C NMR (CDCl₃, JMOD) δ 175.8, 143.4, 137.5, 122.9, 114.4, 59.3, 34.9, 14.3.

Step G. Preparation of Compound (XV)

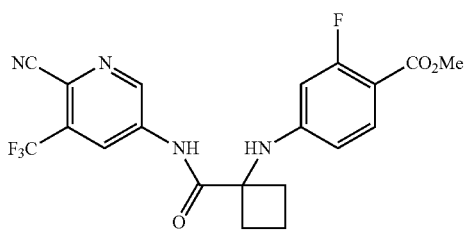

Method A. A solution of 2 g of compound (XIII) in 10 mL of DMA was added over 6 h to a reactor charged with 1.2 eq of compound (XIV)-Cl (X=Cl), 2.5 eq of potassium acetate, 1.0 eq of copper (I) chloride and 5 mL of DMA. The reaction mixture was stirred and heated to 130° C. After 17 h additional stirring, HPLC analysis showed 40% of compound (XV) in the reaction mixture.

Method B. A reactor was charged with 1 g of compound (XIII), 1.18 g of compound (XIV)-I (X=I), 0.7 g of potassium acetate, 0.22 g of copper sponge (1 eq) and 7 mL of DMSO. The mixture was stirred at 25° C. for 7 h. HPLC analysis showed 93% conversion to compound (XV). After addition of EtOH, followed by water and concentrated ammonium hydroxide, compound (XV) was isolated by filtration in 90% yield. ¹H NMR (300 MHz, CDCl₃) δ 10.74 (m, 1H), 9.28 (m, 1H), 8.75 (m, 1H), 7.67 (t, J=2×8.7 Hz, 1H), 7.55 (s, 1H), 7.20 (m, 2H), 6.33 (d, J=8.5 Hz, 1H), 6.18 (d, J=13.8 Hz, 1H), 3.75 (s, 3H) 2.76 (m, 2H), 2.24 (m, 2H), 1.98 (m, 2H); ¹³C NMR (CDCl₃, JMOD) δ 174.6, 164.4, 163.8, 161.1, 151.7, 151.6, 144.7, 139.0, 133.1, 128.8, 128.1, 123.8, 114.7, 109.10, 105.6, 60.6, 51.4, 30.1, 14.40.

Step H. Preparation of Compound (IX)

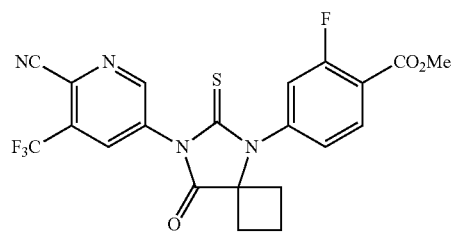

Method A. A reactor was charged with 1 g of compound (XV), 1.1 g of 1,1'-thiocarbonylbis(pyridin-2(1H)-one), 0.56 g of DMAP and 6.2 mL of DMA. The mixture was stirred and heated to 60° C. for 20 h. At that time, 6 mL of EtOH was added, followed by 6 mL of water. The reaction was then cooled to 0° C. Compound (IX) was isolated by filtration in 70% yield. ¹H NMR (300 MHz, DMSO) δ 9.23 (s, J=1.9 Hz, 1H), 8.77 (s, J=2.1 Hz, 1H), 8.18 (t, J=2×8.2 Hz, 1H), 7.58 (dd, J=10.9, 1.7 Hz, 1H), 7.48 (dd, J=8.3, 1.7 Hz, 1H), 3.9 (s, 3H), 2.65 (m, 2H), 2.50 (m, 2H), 2.00 (m, 1H), 1.61 (m, 1H); $^{13}$C NMR (DMSO, JMOD) δ 179.6, 174.2, 163.3, 153.4 (ArH), 140.9, 135.5 (ArH), 132.9 (ArH), 128.9, 126.5 (ArH), 118.9 (ArH), 114.2, 67.7, 52.6 (CH$_3$), 31.2, 13.4.

Method B. A reactor was charged with 0.5 g of compound (XV), 0.35 g (2.5 eq) of DMAP and 5 mL of DMA. The mixture was stirred and cooled to −20° C. To this mixture, phenyl thionochloroformate (0.5 g, 2.5 eq) was added, followed by 0.46 g (4 eq) of triethylamine. The mixture was allowed to warm to room temperature and stirred for 3 h. HPLC analysis showed 97% conversion to compound (IX).

Step I. Preparation of Compound (X) Via Compound (IX)

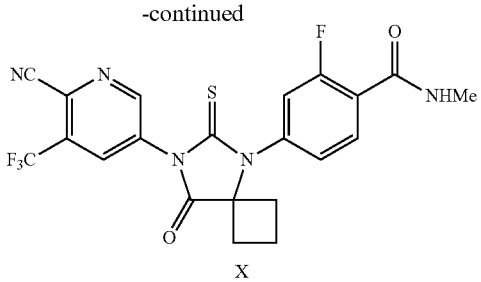

X

A reactor was charged with 0.85 g of Compound (IX). A solution of methylamine in ethanol (8.5 mL) was added and the mixture was stirred at ambient temperature for 3 h. The reaction mixture was then poured into a mixture of 5.1 mL of acetic acid and 19 mL of water. Compound (X) was isolated by filtration in 55% yield. $^1$H NMR (300 MHz, DMSO) δ 9.22 (s, 1H), 8.79 (d, J=1.9 Hz, 1H), 8.52 (m, 1H), 7.83 (t, J=8×2 Hz, 1H), 7.48 (dd, J=10.5, 1.8 Hz, 1H), 7.39 (dd, J=8.2, 1.8 Hz, 1H), 2.8 (d, J=4.5 Hz, 3H), 2.65 (m, 2H), 2.50 (m, 2H), 2.00 (m, 1H), 1.61 (m, 1H).

Example 2

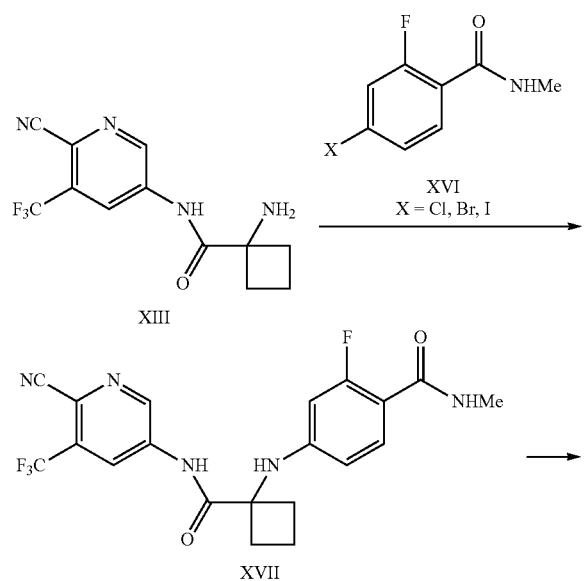

Step A. Preparation of Compound (XVII)

XVII

Method A. To a 1 L reactor was charged with 7.8 g (38 mmol) compound (XVI)-Br (X=Br), 69.7 g (2.5 eq., 79 mmol) of potassium acetate, 12 g (0.3 eq., 9.5 mmol) of copper (I) bromide and 12.8 mL (0.3 eq., 9.5 mmol) of N,N,N',N'-tetramethylethylenediamine and 27 mL of DMA. The mixture was stirred and heated to 120° C. A solution of 9.0 g of compound (XIII) in 12.7 mL of DMA was dosed over 2 h on the hot mixture. After 2 h additional stirring, the mixture was cooled to 60° C. An addition of 27 mL of water followed by 18 mL of acetonitrile was completed. After seeding and aging 1 h, 18 mL of water was dosed slowly over 2 h. The mixture was cooled and then compound (XVII) was isolated by filtration in 84% yield. $^1$H NMR (300 MHz, DMSO) δ 10.7 (s, 1H), 9.3 (s, 1H), 8.74 (s, 1H), 7.73 (m, 1H), 7.47 (m, 1H), 7.19 (s, 1H), 6.30 (d, J=8.3 Hz, 1H), 6.10 (d, J=13.9 Hz, 1H), 2.70 (m, 3H), 2.70 (m), 2.17 (m), 1.95 (m); $^{13}$C NMR (DMSO, JMOD) δ 175.0, 163.7, 162.3, 159.1, 149.6, 149.4, 144.6 (ArH), 139.0, 131.5 (ArH), 129.4, 129.0, 123.6 (ArH), 122.4, 120.0, 114.7, 111.4, 111.2, 109.2 (ArH), 99.5 (ArH), 60.6, 30.1, 26.2, 14.3.

Method B. A reactor was charged 500 mg of compound (XIII), 1.1 equivalents of compound (XVI)-Br (X=Br), 1 equivalent of copper powder, 2.0 equivalents of potassium acetate and 2.5 mL of DMSO. The mixture was stirred and heated to 60° C. for 18 h, after which the HPLC showed that 80% of compound XVII was formed.

Step B. Preparation of Compound (X) from Compound (XVII).

Method A. A reactor was charged with 48 g of Compound (XVII), 52.8 g of 1,1'-thiocarbonylbis(pyridin-2(1H)-one), 13.5 g of 4-dimethylaminopyridine and 144 mL of DMA. The mixture was stirred and heat to 90° C. for 2 h. The reaction was then cooled to 60° C. A volume of 37 mL of HCl (6 M in isopropanol) was added, followed by 144 mL of isopropanol and 216 mL of water. Compound (X) was isolated by filtration in 80% yield.

Method B.

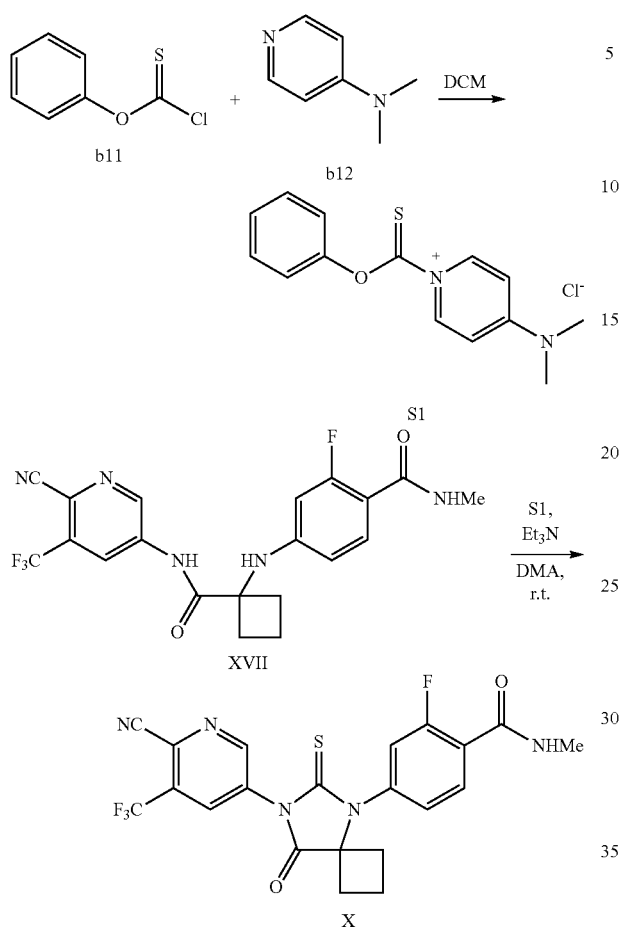

A portion of DMAP (b12, 2.0 g) was dissolved in 20 mL DCM and cooled to −30° C. Phenyl thionochloroformate (b11, 4.3 g, 1.5 eq) was added and the mixture stirred for 1 h. The mixture was filtered and the collected solid was dried at room temperature under reduced pressure to give 4.3 g of quaternary salt (S1) as a crystalline yellow product. $^1$H NMR (400 MHz, CD$_3$CN): 3.39 (6H, s), 7.04 (2H, d), 7.29 (2H, d), 7.44 (1H, t), 7.58 (2H, t), 9.04 (2H, d).

Compound (XVII) (0.5 g, 1.1 mmol) and triethylamine (0.93 g, 8.8 mmol) were dissolved in 5 mL DMA at 21° C. Salt S1 (0.81 g, 2.75 mmol) was added and the solution stirred at room temperature. Analysis of the solution by HPLC after 1 h showed 38% conversion to Compound (X).

Method C. DMAP (4.41 g, 2.2 eq, 36.1 mmol) was dissolved in 107 mL of ethyl acetate and heated to 60° C. Compound (XVII) (7.15 g, 16.4 mmol) was added followed by distillation of 35 mL of ethyl acetate to remove water. At 50° C., 6.24 g (2.2 eq., 36.1 mmol) of phenyl thionochloroformate was added and the mixture was stirred for 1 h before addition of 9.16 mL (65.7 mmol) of triethylamine. The reaction was kept at 50° C. for 6 h, then cooled to 5° C. 13.7 mL (5 eq., 82.1 mmol) of 6 M hydrochloric acid in 2-propanol was added. The mixture was then washed with 35.8 mL of water, followed by a brine wash. The resulting organic layer was evaporated and replaced with toluene and n-butanol. After seeding, the mixture was cooled and compound (X) was collected by filtration, washed and dried. Yield: 72%.

Method D. DMAP (15.4 g, 2.2 eq) was dissolved in 250 mL of ethyl acetate. Compound (XVII) (25 g) was added followed by heating to 50° C. Phenyl thionochloroformate (2.2 eq.) was added and the mixture was stirred for 1 h before the addition of 32 mL (4.0 eq) of triethylamine. The reaction temperature was maintained at 50° C. for 6 h, then cooled to 20° C. N,N-dimethylpropane-1,3-diamine (DMAPA) (2 eq.) was added and the mixture was stirred for 5 h. 6 M hydrochloric acid in 2-propanol (125 mL) was added and stirred for 2 h at 30° C. The organic layer was then washed with 125 mL of water. The resulting organic layer was concentrated and replaced with n-butanol. After seeding, the mixture was cooled and compound (X) was collected by filtration, washed, and dried. Yield: 79%.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A process for the preparation of compound (X)

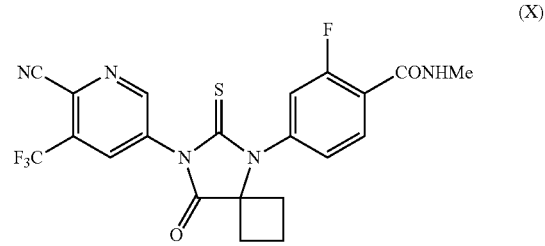

comprising

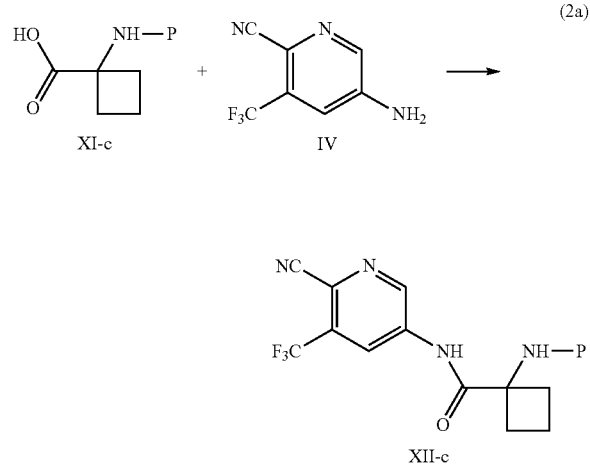

reacting a compound of formula (XI-c), wherein P is an amino protecting group, with compound (IV); in the presence of an amide coupling reagent; and in the presence of a catalyst; in an organic solvent; at a temperature in the range of from about 0° C. to about 50° C.; to yield the corresponding compound of formula (XII-c); or,

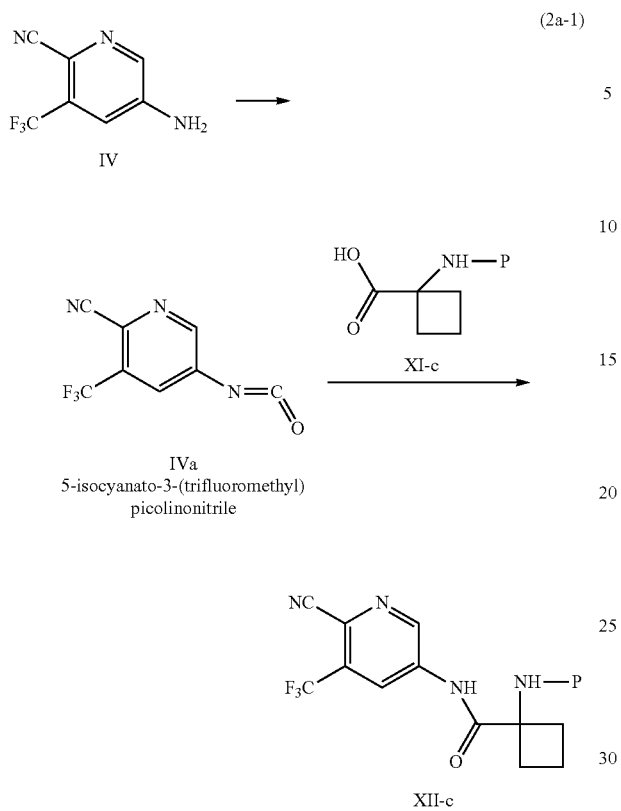

(2a-1)

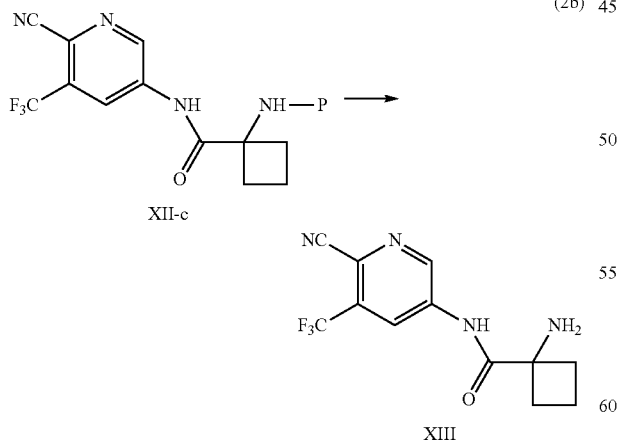

reacting compound (IV) with phosgene or a phosgene analog; in the presence of an organic base; in an aprotic solvent; then treating a resulting isocyanate intermediate (IVa), optionally without isolation, with a compound of formula (XI-c); in the presence of a non-nucleophilic base; at a temperature in the range of from about −20° C. to about 80° C.; to yield the corresponding compound of formula (XII-c);

(2b)

reacting a compound of formula (XII-c) under amino deprotection conditions; in an organic solvent; at a temperature greater than ambient temperature; to yield the corresponding compound (XIII);

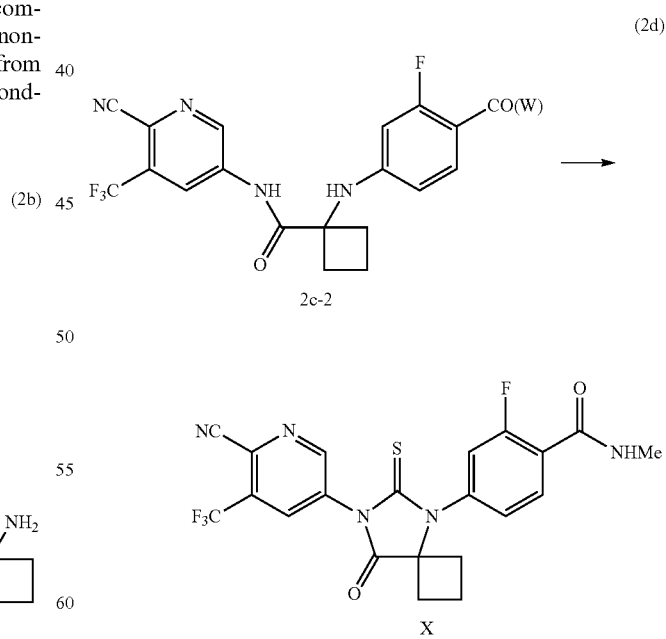

reacting compound (XIII) with a compound of formula (2c-1) wherein X is chloro, bromo, or iodo, and W is $C_{1-8}$alkoxy or methylamino; in the presence of a copper (0) source or a copper salt; in the presence of an inorganic base; in an organic solvent; optionally in the presence of a ligand; optionally in the presence of a reducing agent; at a temperature in the range of from about room temperature to about 140° C.; to yield the corresponding compound of formula (2c-2) wherein W is $C_{1-8}$alkoxy (2c-2B) or methylamino (XVII);

(2d)

reacting a compound of formula (2c-2) to form compound (X).

2. The process of claim 1 wherein step (2a) further comprises

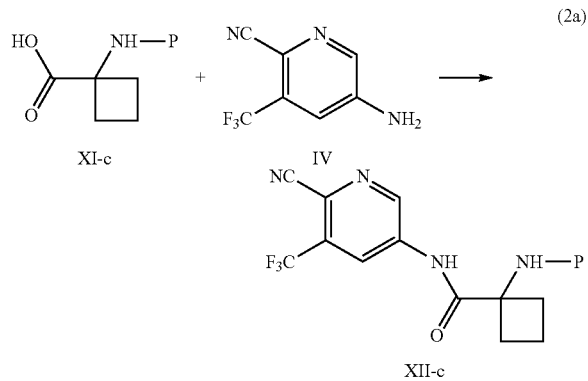

reacting a compound of formula (XI-c), wherein P is an amino protecting group, with compound (IV); in the presence of an amide coupling reagent selected from the group consisting of 1,1-carbonyldiimidazole, T3P, EDCI, DMTMM, and EEDQ; in the presence of a catalyst selected from the group consisting of DBU, DBN, DABCO, triethylamine, DIPEA, TBD, TMG, MTBD, NaH, KOtBu, and LiHMDS; in an organic solvent selected from the group consisting of toluene, MeTHF, THF, iPrOAc, DCM, and IPA; at a temperature in the range of from about 0° C. to about 50° C.; to yield the corresponding compound of formula (XII-c).

3. The process of claim 2 wherein the amide coupling agent is 1,1-carbonyldiimidazole and the catalyst is DBU.

4. The process of claim 1 wherein step (2a-1) further comprises

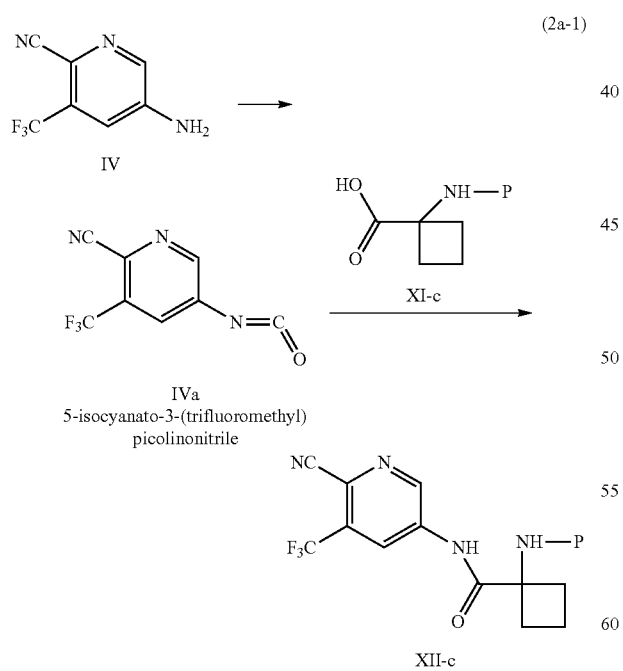

reacting compound (IV) with phosgene or a phosgene analog selected from the group consisting of triphosgene (bis(trichloromethyl) carbonate) and diphosgene (trichloromethyl chloroformate); in the presence of an organic base selected from the group consisting of triethylamine, ethyl diisopropylamine, and DABCO; in an aprotic solvent that is DCM, toluene, THF, or MeTHF; at a temperature in the range of from about −20° C. to about 50° C.; to form an isocyanate intermediate (IVa); then reacting said isocyanate intermediate (IVa) with a compound of formula (XI-c); in the presence of a non-nucleophilic base selected from the group consisting of DBU, DBN, DABCO, triethylamine, TBD, TMG, and MTBD; at a temperature in the range of from about −20° C. to about 80° C.; to yield the corresponding compound of formula (XII-c).

5. The process of claim 1 wherein step (2c) further comprises

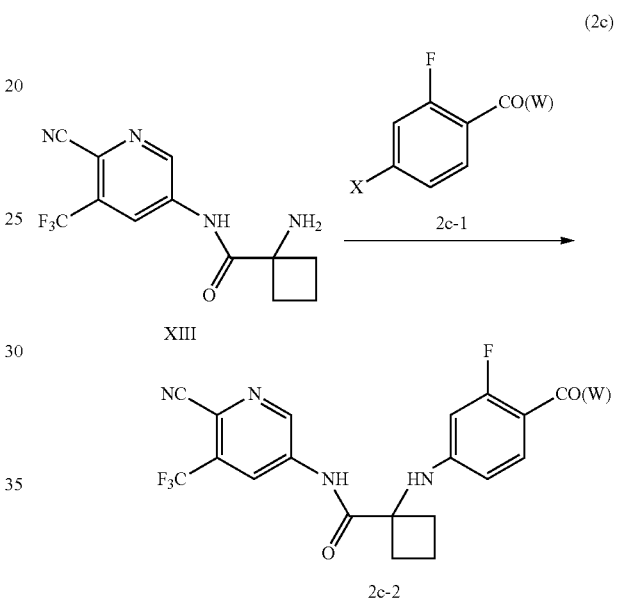

reacting compound (XIII) with a compound of formula (2c-1) wherein X is chloro, bromo, or iodo, and W is $C_{1-8}$alkoxy or methylamino; in the presence of either (1) a copper (0) source that is copper powder or copper sponge, or (2) a copper salt selected from the group consisting of cuprous chloride, cuprous iodide, cuprous bromide, cuprous acetate, and cupric bromide; in the presence of an inorganic base selected from the group consisting of potassium acetate, potassium carbonate, cesium carbonate, and CsF; in an organic solvent that is DMF, DMA, DMSO, acetonitrile, propionitrile, butyronitrile, or amyl alcohol; with or without the addition of a copper (I) salt selected from the group consisting of cuprous chloride, cuprous iodide, cuprous bromide, and cuprous acetate; and, optionally in the presence of a ligand selected from the group consisting of 2-acetylcyclohexanone, TMEDA, and phenanthroline; also, optionally in the presence of a reducing agent that is sodium ascorbate or sodium bisulfite; at a temperature in the range of from about room temperature to about 140° C.; to yield the corresponding compound of formula (2c-2) wherein W is $C_{1-8}$alkoxy (2c-2B) or methylamino (XVII).

6. The process of claim 5, comprising reacting compound (XIII) with a compound of formula (2c-1) in the presence of cuprous bromide; in the presence of TMEDA; in the presence of potassium acetate; in organic solvent DMA; at a temperature in the range of from about 80° C. to about 140° C.

7. The process of claim 5, comprising reacting compound (XIII) with a compound of formula (2c-1) in the presence of a copper (0) source that is copper powder or copper sponge; in the presence of potassium acetate or sodium pivalate; in organic solvent DMSO; at a temperature in the range of from about 0° C. to about 80° C.

8. The process of claim 5, comprising reacting compound (XIII) with a compound of formula (2c-1) in the presence of a copper (0) source that is copper powder or copper sponge; in the presence of potassium acetate; with the addition of a copper (I) salt selected from the group consisting of cuprous chloride, cuprous iodide, cuprous bromide, and cuprous acetate; in organic solvent DMSO; at a temperature in the range of from about 0° C. to about 80° C.

9. The process of claim 1, wherein step (2d) further comprises the reaction of compound (XVII) to form compound (X) by

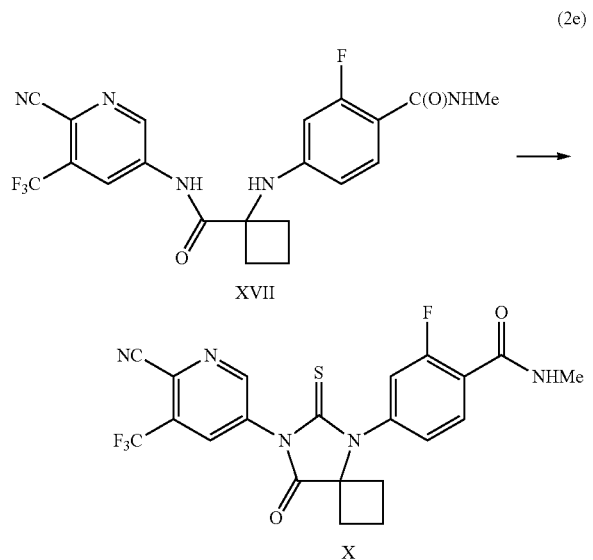

reacting compound (XVII) with a thiocarbonyl source; in the presence of an activating agent; in an organic solvent; optionally in the presence of an organic base; at a temperature in the range of from about −20° C. to about 100° C.; to yield the corresponding compound (X).

10. The process of claim 9, wherein step (2e) further comprises reacting compound (XVII) with a thiocarbonyl source selected from the group consisting of O,O'-di(pyridin-2-yl)carbonothioate, 1,1'-thiocarbonylbis(pyridin-2(1H)-one), di(1H-imidazol-1-yl)methanethione, thiophosgene, phenyl thionochloroformate, O-(2-naphthyl) thionochloroformate, tolyl thionochloroformate, and thiocarbonyl bis(benzotriazole); in the presence of an activating agent selected from the group consisting of DMAP, NaH, and NaOH; in an organic solvent selected from the group consisting of DMA, DMF, toluene, DMSO, ACN, THF, DCM, EtOAc, acetone, MEK, and dioxane; optionally in the presence of an organic base selected from triethylamine or DIPEA; at a temperature in the range of from about −20° C. to about 100° C.; to yield the corresponding compound (X).

11. The process of claim 10 wherein the thiocarbonyl source is 1,1'-thiocarbonylbis(pyridin-2(1H)-one).

12. The process of claim 11 wherein the activating agent is DMAP.

13. The process of claim 12 wherein the organic solvent is DMA.

14. The process of claim 10 wherein the thiocarbonyl source is phenyl thionochloroformate; the activating agent is DMAP; the organic base is triethylamine or DIPEA; the organic solvent is DMA; at a temperature in the range of from about −20° C. to about 80° C.

15. The process of claim 10 wherein the thiocarbonyl source is phenyl thionochloroformate; the activating agent is DMAP; the organic base is triethylamine or DIPEA; the organic solvent is acetone or ethyl acetate; at a temperature in the range of from about −20° C. to about 80° C.

16. The process of claim 15 wherein immediately after cyclization, DMAPA is added.

17. The process of claim 10, wherein step (2e) further comprises reacting phenyl thionochloroformate with DMAP to form an isolatable quaternary salt, compound (S1),

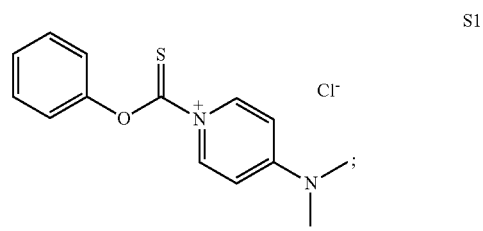

then, reacting compound (XVII) with compound S1; in the presence of an organic base selected from triethylamine or DIPEA; in DMA; at a temperature in the range of from about −20° C. to about 80° C.; to yield the corresponding compound (X).

18. The process of claim 1, wherein step (2d) further comprises the conversion of a compound of formula (2c-2B) to a compound of formula (2e), by

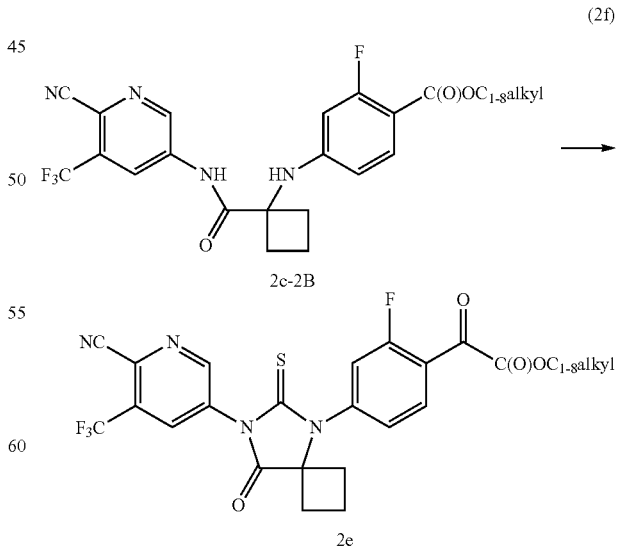

reacting a compound of formula (2c-2B) with a thiocarbonyl source; in the presence of an activating agent; in an organic solvent; at a temperature in the range of from about −20° C. to about 100° C.; to yield the corresponding compound of formula (2e); then,

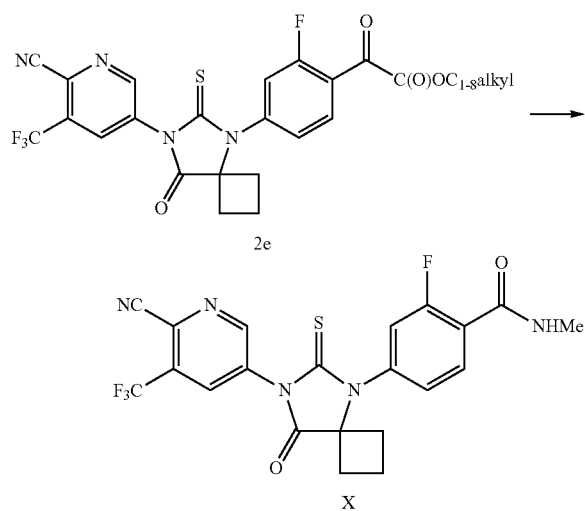

treating a compound of formula (2e) with methylamine; in an organic solvent; at about ambient temperature; to yield the corresponding compound (X).

19. The process of claim 18, further comprising reacting a compound of formula (2c-2B) with a thiocarbonyl source selected from the group consisting of O,O'-di(pyridin-2-yl)carbonothioate, 1,1'-thiocarbonylbis(pyridin-2(1H)-one), di(1H-imidazol-1-yl)methanethione, thiophosgene, phenyl thionochloroformate, O-(2-naphthyl) thionochloroformate, tolyl thionochloroformate, and thiocarbonyl bis(benzotriazole); in the presence of an activating agent selected from the group consisting of DMAP, NaH, and NaOH; in an organic solvent selected from the group consisting of dimethylacetamide, DMF, toluene, DMSO, THF, and dioxane; at a temperature in the range of from about −20° C. to about 100° C.; to yield the corresponding compound of formula (2e); then
treating the compound of formula (2e) with methylamine; in an organic solvent selected from the group consisting of THF, DMF, DMA, ethanol, and an aqueous mixture thereof; at about ambient temperature; to yield the corresponding compound (X).

20. The process of claim 19 wherein treating the compound of formula (2e) with methylamine further comprises using ethanol as the organic solvent.

21. The process of claim 19 further comprising reacting a compound of formula (2c-2B) wherein the thiocarbonyl source is phenyl thionochloroformate; the activating agent is DMAP; the organic solvent is acetone or ethyl acetate; at a temperature in the range of from about −20° C. to 40° C.; to yield the corresponding compound of formula (2e); then, treating the compound of formula (2e) with methylamine; in ethanol; at about room temperature; to yield the corresponding compound (X).

22. The process of claim 18, wherein step (2f) further comprises reacting phenyl thionochloroformate with DMAP to form an isolatable quaternary salt, compound (S1),

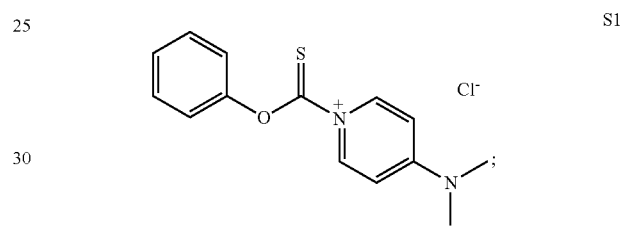

then,
reacting compound (2c-2B) with compound S1; in the presence of an organic base selected from triethylamine or DIPEA; in DMA; at a temperature in the range of from about −20° C. to about 80° C.; to yield the corresponding compound (X).

* * * * *